United States Patent
Daugherty et al.

[11] Patent Number: 5,950,986
[45] Date of Patent: Sep. 14, 1999

[54] VALVED PRN ADAPTER FOR MEDICAL ACCESS DEVICES

[75] Inventors: Charles W. Daugherty, Jamestown, Ohio; Timothy J. Erskine; Glade Howell, both of Sandy, Utah

[73] Assignee: Becton, Dickinson and Company, Franklin, N.J.

[ * ] Notice: This patent is subject to a terminal disclaimer.

[21] Appl. No.: 09/014,904

[22] Filed: Jan. 28, 1998

Related U.S. Application Data

[63] Continuation of application No. 08/624,241, Mar. 29, 1996, Pat. No. 5,776,113.

[51] Int. Cl.$^6$ .................................................. A61M 25/00
[52] U.S. Cl. ...................... 251/149.6; 604/280; 604/246
[58] Field of Search .............................. 251/149.6, 149.1; 604/280, 283, 246, 905, 247

[56] References Cited

U.S. PATENT DOCUMENTS

| | | | |
|---|---|---|---|
| 2,265,267 | 12/1941 | Cowles | 251/149.6 |
| 2,412,685 | 4/1946 | Hoffman et al. | 251/149.6 |
| 3,352,531 | 11/1967 | Kilmarx . | |
| 3,825,222 | 7/1974 | Petrova | 251/149.6 |
| 4,512,766 | 4/1985 | Vaillancourt . | |
| 4,645,494 | 2/1987 | Lee et al. . | |
| 4,874,377 | 10/1989 | Newgard et al. . | |
| 5,085,645 | 2/1992 | Purdy et al. . | |
| 5,108,380 | 4/1992 | Herlitze et al. . | |
| 5,122,123 | 6/1992 | Vaillancourt . | |
| 5,203,775 | 4/1993 | Frank et al. . | |
| 5,242,393 | 9/1993 | Brimhall et al. . | |
| 5,251,873 | 10/1993 | Atkinson et al. . | |
| 5,269,771 | 12/1993 | Thomas et al. . | |
| 5,273,533 | 12/1993 | Bonaldo . | |
| 5,306,243 | 4/1994 | Bonaldo . | |
| 5,380,306 | 1/1995 | Brinon . | |
| 5,470,319 | 11/1995 | Mayer . | |
| 5,474,536 | 12/1995 | Bonaldo . | |
| 5,487,728 | 1/1996 | Vaillancourt . | |
| 5,509,912 | 4/1996 | Vaillancourt . | |
| 5,514,116 | 5/1996 | Vaillancourt et al. . | |
| 5,520,666 | 5/1996 | Choudhury et al. . | |
| 5,549,566 | 8/1996 | Elias et al. . | |
| 5,549,577 | 8/1996 | Siegel et al. . | |
| 5,616,130 | 4/1997 | Mayer . | |

FOREIGN PATENT DOCUMENTS

| | | |
|---|---|---|
| 0 087 901 A2 | 9/1983 | European Pat. Off. . |
| 0 307 771 | 4/1989 | European Pat. Off. . |
| 0 639 389 A1 | 2/1995 | European Pat. Off. . |
| 0 748 635 A2 | 12/1996 | European Pat. Off. . |
| WO 93/11828 | 6/1993 | WIPO . |
| WO 96/00107 | 1/1996 | WIPO . |

*Primary Examiner*—Kevin Lee
*Attorney, Agent, or Firm*—Eric M. Lee

[57] ABSTRACT

A valved adapter for connecting a fluid handling device to a medical device includes a body with a longitudinal axis having a proximal end, a distal end and a chamber therewithin. The body includes a passageway from the proximal end to the distal end and has a valve contained within the chamber in a normally closed position that is operative to an open position. The valve also includes a hollow tube having a bore therethrough with a closed proximal end mounted coaxially within the passageway and extending from the proximal end to the distal end of the body. The tube has at least one side port opening into its bore that is located a distance distally from the closed end. The valve also includes a resilient member located coaxially about the tube that is biased to occlude the side port in the valve's normally closed position. The valve is opened by a distal movement of the resilient member to overcome the bias and to uncover the side port thereby allowing a fluid flow into the tube and through the valve.

5 Claims, 4 Drawing Sheets

VALVED PRN ADAPTER FOR MEDICAL ACCESS DEVICES

This application is a continuation of application Ser. No. 08/624,241, filed Mar. 29, 1996, now U.S. Pat. No. 5,776,113.

FIELD OF INVENTION

The present invention relates to infusion devices and more particularly to a valved adapter useful with a variety of medical access devices.

BACKGROUND

Medical access devices, particularly infusion devices, over-the-needle catheters, other catheters and feeding tubes are important tools for administration of fluids to patients. After placement, in normal management of a catheter or other medical access device in a patient, it is often necessary to be able to add or withdraw fluids through the device. In many surgical procedures, it is routine to place an intravenous catheter so that if it is necessary to medicate a patient during a procedure, the catheter already is in place. In other types of procedures it is necessary to periodically administer medicaments through the device or to withdraw samples. In all of these applications, the presence of a valve mechanism on the device to facilitate the addition and to close the device after the addition is desirable.

U.S. Pat. No. 4,512,766 discloses an intravenous catheter assembly with a valve located in the catheter hub made of needle-penetrable self-sealing material such as an elastomeric cap with a closed end. The valve disclosed in the patent is biased to a closed position wherein it surrounds an open inlet end of a hollow elongated insert tube disposed in the hub. The valve may be opened by positioning a male luer adapter onto the assembly. The male luer adapter forces the elastomeric cap to slide longitudinally along the insert tube past the insert tube open end. As the elastomeric cap moves, a puncture or slit previously placed in the wall of the closed end of the elastomeric cap expands over the insert tube open end as the cap is collapsed axially. The insert tube open end then projects into the male luer adapter so that fluid may pass into the insert tube. When the male adapter is removed, the compressed elastomeric cap expands and closes the puncture or slit over the open end of insert tube to close the valve.

U.S. Pat. No. 5,085,645 teaches an over-the-needle catheter having an integral valve in a passage in the catheter hub. The patent discloses a valve adapter that is an integral part of a catheter hub.

U.S. Pat. No. 5,251,873 teaches a medical coupling site that is adapted to be attached directly to a standard male luer lock fitting. The coupling site includes a valve element contained within a tubular retainer. The coupling site includes a slit rubber diaphragm valve that is deflected and opened by introduction of a male luer fitting and closed by the removal of the male luer. According to international standards, there is an allowable range of 2.5 mm in engagement length of a luer fitting. This variation in engagement length occurs because of variation in the outside diameter of the male projection and the inside diameter of the female receptacle of the luer fittings. Thus, a "fat" male luer results in a "short" engagement length and conversely. Valves of the type disclosed in U.S. Pat. No. 5,251,873 may not open fully with male luer fittings at the "short" end of the allowable dimension, and since they also depend on the diaphragm for sealing around the male luer tip, they may also leak when a male fitting is mounted or may not fully close once opened.

U.S. Pat. No. 5,108,380 discloses a valve device for a hub member of a catheter. The valve is actuated by the placement of a male luer fitting which displaces a piston biased by a coil spring to open the valve.

U.S. Pat. No. 5,269,771 discloses a needleless introducer with a hemostatic valve. The valve mechanism includes a plunger biased by a coil spring that, upon actuation, spreads a pair of resilient valve elements. A valve of the design disclosed in this patent may not be fully opened by a male luer fitting at the "short" side of the dimension, and the sealing depends upon the resilient valve elements closing against themselves. Further, the valve disclosed in this patent is composed of several different materials and is complex to assemble.

Valves and adapters of the type described above fall into a medical device category often referred to as "PRN" from the Latin pro re nata, i.e., as the circumstances may require. A typical example of usage for this type device is on a catheter left in place for three days. During this three day usage duration, a bolus dosage of a medicament might be given every 4 hours using a protocol including at each dosage interval: a) flushing the catheter to check patency; b) administration of the medicament; and c) flushing the medicament from the catheter with heparin or saline. During this typical usage period, this protocol results in 54 operations of the valve, i.e., 6 times a day, 3 steps each time and 3 days. Between each dosage the valve must not leak, but it must be readily reopened. Following the traditional technique, bolus introductions would have been made using hypodermic needles to penetrate a resilient septum. However, a septum is likely to start leaking after multiple penetrations and, given the concerns about risks to practitioners and service personnel from "sharps," hospitals have changed many protocols to reduce the use of pointed hypodermic needles. The PRN adapters as described above have been developed to address the hospitals' changing needs.

While the teachings cited above address many of the practitioners' concerns, there is still a need for a valved adapter for medical access devices that offers rapid, easy-to-use access with automatic positive on/off flow control. Additionally, many of the currently available adapters are open at the proximal end requiring an additional plug or cover to avoid contamination of the fitting when a fluid delivery device is not mounted. A device having these features plus the advantage of being self closing, easily cleanable and simple to manufacture is disclosed herein.

SUMMARY

A valved adapter for connecting a fluid handling device to a medical device of the present invention includes a body with a longitudinal axis, a proximal end with a proximal surface, a distal end and a chamber therewithin. The body includes a passageway from its proximal end to the distal end. The adapter of the invention includes a valve contained within the chamber in a normally closed position but being operative to an open position. The valve includes a hollow tube with a bore therethrough and a closed proximal end. The tube is mounted coaxially within the passageway extending from the proximal end of the body to the distal end. The tube has at least one side port opening into the bore located a distance distally from the closed end. The valve further includes a resilient member located coaxially about the tube biased to occlude the side port in the normally closed position. The valve is opened by distal movement of the resilient member to overcome the bias and to uncover the side port thereby to allow a fluid flow through the valve.

The adapter of the present invention, by having the resilient member close the side port of the tube as the resilient member returns to the normally closed position as the fluid handling device is removed, substantially eliminates the tendency of many valved adapters to spurt liquid present on the surface of the valve mechanism. Fluid handling devices generally are attached to the valve adapter with a male luer fitting With the present invention, by the time a fluid handling device is fully removed from the adapter, the side port opening is already occluded. Additionally, because the volume of the liquid present on the surface of the resilient member is very small, there is substantially no spurting. The adapter of the present invention has an easily cleaned proximal surface that may be wiped substantially clean by a user when the fluid handling device is removed. The adapter of the present invention has substantially no "dead volume" between the normally closed valve and the proximal surface of the adapter, thereby substantially avoiding residual material that may support microbial growth or occlude the valve during periods when the valve is not in use.

DETAILED DESCRIPTION

Figure 1:
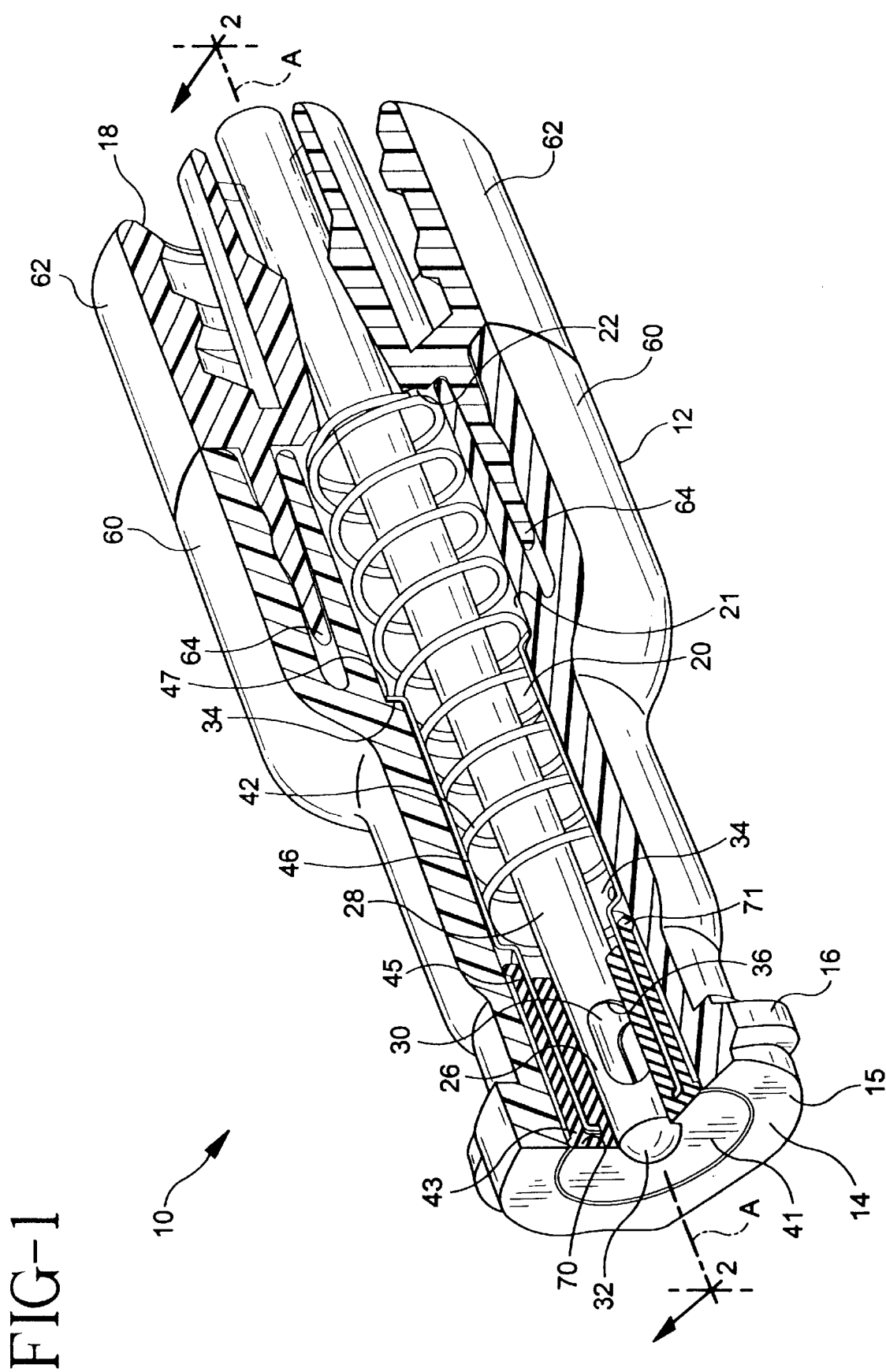
FIG. 1 is a cut-away perspective view of a preferred embodiment of the valved adapter of the present invention.

While this invention is satisfied by embodiments in many different forms, there are shown in the drawings and herein described in detail preferred embodiments of the invention with the understanding that the present disclosure is to be considered exemplary of the principles of the invention and is not considered to limit the invention to the embodiments illustrated. The scope of the invention is measured by the appended claims and their equivalents. In this description, the term "proximal" refers to the end of the adapter closest to the user, with the term "distal" referring to the end of the adapter away from the user.

Figure 2:
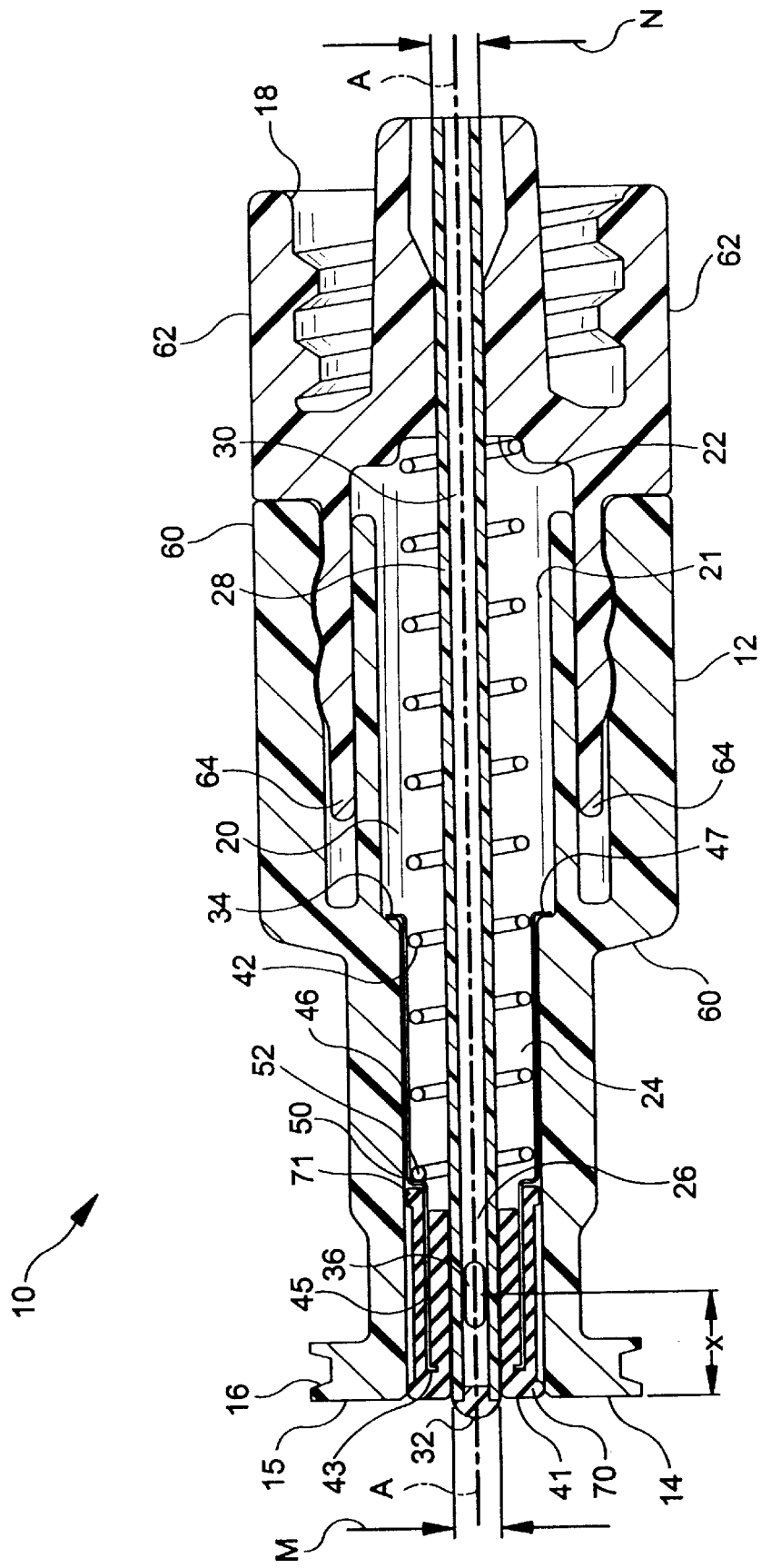
FIG. 2 is a cross-sectional view of the adapter of FIG. 1 taken along the line 2—2.
Figure 3:
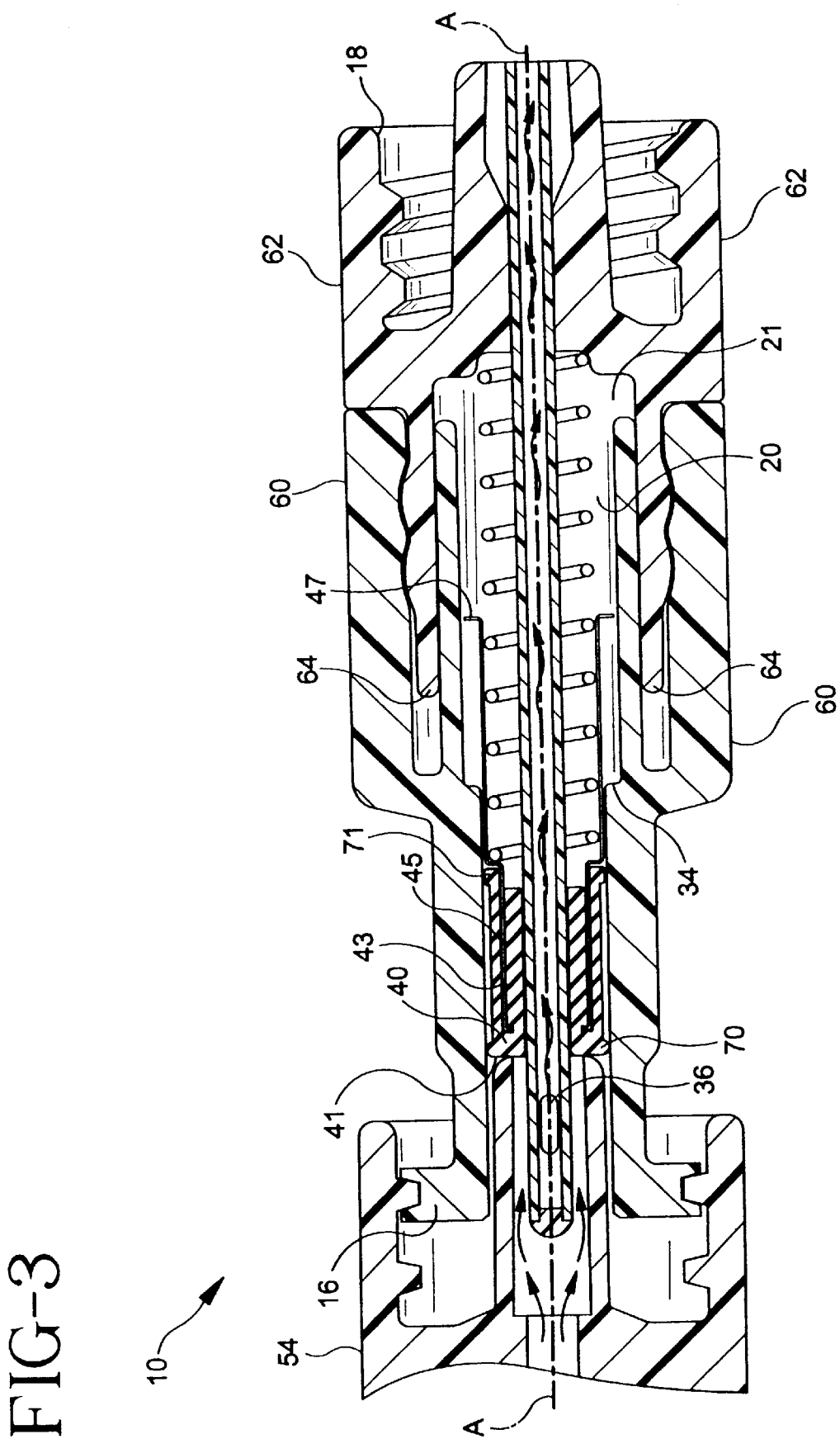
FIG. 3 is a cross-sectional view of the adapter of FIG. 1, analogous to FIG. 2, with a male luer fitting mounted on its proximal end.

Referring to FIGS. 1–3, a preferred valved adapter 10 of the present invention for connecting a fluid handling device to a medical device includes a body 12, with a longitudinal axis A, that has a proximal end 14 and a proximal surface 15, preferably with a female luer fitting 16, a distal end 18 and a chamber 20 therewithin that has an inside surface 21 and an inwardly projecting distal shoulder 22. Body 12 includes a passageway 24 from proximal end 14 to distal end 18. Adapter 10 has a valve 26 contained within chamber 20 in a normally closed position as shown in FIGS. 1 and 2 that is operative to an open position as shown in FIG. 3. Valve 26 includes a hollow tube 28 with a bore 30. Tube 28 has a closed proximal end 32 that may be flat or domed. Tube 28 is mounted coaxially within passageway 24 and extends from proximal end 14 of the body preferably to distal end 18. Passageway 24 also includes an inward step 34 intermediate proximal end 14 and shoulder 22. As shown in FIG. 1, preferred tube 28 has two side ports 36 opening into bore 30 that are located a distance "x" distally from closed end 32 of the tube, but one or more side port openings are also satisfactory. Preferably, side port openings 36 are generally oval, although the shape of the opening may vary. Valve 26 also includes a resilient member 40 coaxially about tube 28 so that a proximal surface 41 of the resilient member is approximately adjacent closed proximal end 32 of the tube. Valve 26 preferably has a helical coil spring 42, formed from a biocompatible metal such as stainless steel, located distally to resilient member 40 and coaxially about tube 28. Resilient member 40 also preferably includes a reinforcement 46 with a ledge 50 to accept a proximal end 52 of spring 42. Preferred spring 42 is compressible between ledge 50 and shoulder 22 to provide a bias so that resilient member 40 occludes side ports 36 in the normally closed position.

Preferably, reinforcement 46 includes an extension section 45 fit within a recess 43 in resilient member 40. The reinforcement preferably also has a guide flange 47 to contact interior surface 21 of chamber 20 during the axial movement of resilient member 40 to open and close valve 26. Guide flange 47 is limited in proximal travel by contact with step 34 providing a limit to the proximal movement of the resilient member. In addition to providing the ledge to support spring 42, reinforcement 46 serves to direct and facilitate the opening and closing of the valve, substantially eliminating mis-alignment of the resilient member that could cause binding and sticking of the valve. Reinforcement 46 may be formed from substantially rigid polymeric materials such as polycarbonate, polyacetal, polystyrene and the like as well as biocompatible metals such as stainless steels. Preferably, reinforcement 46 is formed from polycarbonate.

Referring now to FIG. 3, resilient member proximal surface 41 is preferably contacted and resilient member 40 moved distally by a male luer fitting 54 mounted on preferred female luer fitting 16. Preferably, resilient member 40 is sufficiently compliant to form a substantially fluid tight seal with the male luer fitting at proximal surface 41. Valve 26 is opened by the distal movement of resilient member 40 from the normally closed position, as illustrated in FIGS. 1 and 2, to overcome the bias and to uncover side ports 36 and, as illustrated by the flow arrows, to allow a fluid flow through the valve. Resilient member 40 preferably includes a proximal seal 70 and a distal seal 71, each preferably formed as a feather edge. These seals are dimensioned to contact the inside surface of the passageway and substantially prevent fluid from entering the chamber distal to the resilient member. The proximal seal also serves to provide substantially continuous surface 15 to the valved adapter.

From study of FIG. 3 that shows a male luer fitting of a fluid handling mounted on adapter 10 to open the valve, it is apparent that side ports 36 are occluded by resilient member 40 before the male luer fitting is fully dismounted. Thus, as fluid handling device is being dismounted, the male luer fitting continues to obstruct the fluid pathway after the valve is closed. Since valve 36 is already fully closed before the fluid handling device is fully dismounted, there is little probability of backflow leakage through the adapter. Additionally, when any adapter is used to connect a syringe to a catheter in a blood vessel and the contents of the syringe are expelled, a continuous liquid column exists from the syringe to the open end of the catheter in the blood vessel. When the syringe is removed, if a prior adapter was in use, the volume of the liquid column present in the syringe tip is removed from the column resulting in a like volume of blood being drawn back into the catheter. This "backflow" blood may clot and cause blockage in a subsequent use of the catheter. In the adapter of the present invention, there is substantially no movement of liquid in the valve as the side port is occluded, substantially eliminating any drawback of blood into the catheter as the syringe is removed. Further, the mode of closing the valve, distal movement of resilient member 40 to occlude opening 36, is less likely to propel a droplet when compared to a diaphragm or poppet valve-type closure used in many other valves.

The use of resilient member 40 to occlude side port 36 to close valve 26 also substantially eliminates the problem of leakage at the seal that is evident in many of the prior valves that use resilient closures. Many of the prior valves involve a penetration of a resilient closure portion by a piercing member or spreading of a slit to open the valve. Valves that use such a penetration to open the valve generally must depend on a resealing of the penetration or a closing of the slit to seal off the valve. After repeated operating cycles of these valves, as required in many clinical applications, they may have a tendency to leak or weep at the slit or penetration point.

Body 12 preferably is formed of separate proximal part 60 and a distal part 62 that are joined at a snap fit joint 64 as the valve is positioned within the chamber, as shown in FIGS. 1–3. Other suitable methods of attaching proximal part 60 to distal part 62 include, but are not limited to, adhesive bonding, solvent bonding, ultrasonic welding and the like. Suitable materials for forming body 12 include, but are not limited to, polyester, polypropylene, polyvinylchloride, polyamide, polycarbonate, polysulfone, polyacetal, acrylonitrile-butadiene-styrene (ABS), polyacrylate and the like. Preferably, body 12 is formed from polypropylene.

Figure 4:
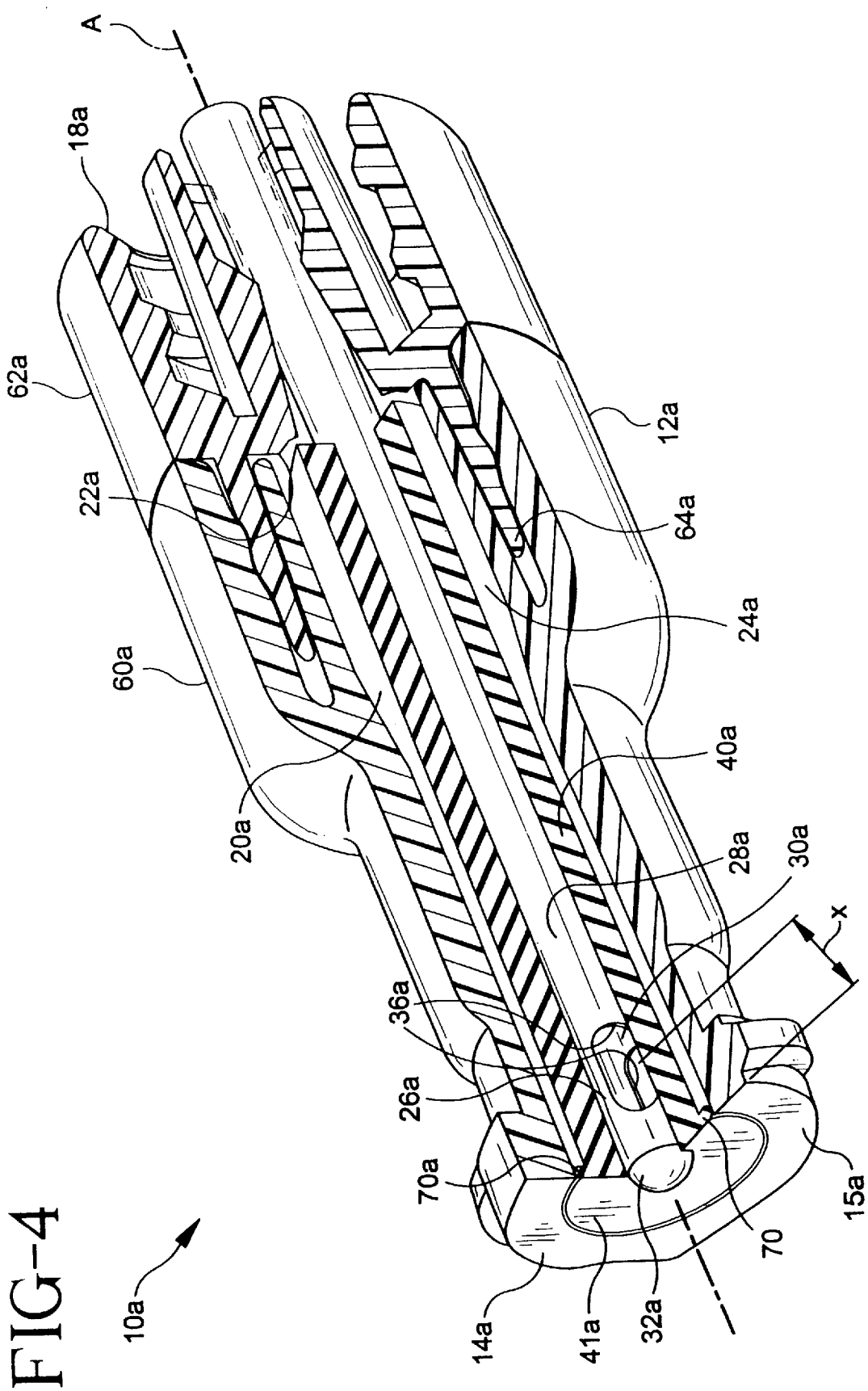
FIG. 4 is a cut-away perspective view of an alternative embodiment of the valved adapter of the present invention.

Referring to FIG. 4, an alternative embodiment of the adapter of the present invention is illustrated. In this embodiment, the structure of the adapter is substantially similar to the adapter of FIGS. 1–3. Accordingly, substantially similar components that perform substantially similar functions are numbered identically to those components of FIGS. 1–3, except that a suffix "a" is used to identify those components in FIG. 4.

As illustrated in FIG. 4, a valved adapter 10a of the present invention for connecting a fluid handling device to a medical device includes a body 12a with a longitudinal axis A having a proximal end 14a, a distal end 18a, and a chamber 20a therewithin that has an inwardly projecting distal shoulder 22a. Body 12a includes a passageway 24a from proximal end 14a to distal end 18a. Adapter 10a has a valve 26a contained within chamber 20a in a normally closed position that is operative to an open position. Valve 26a includes a hollow tube 28a with a bore 30a therethrough. Tube 28a has a closed proximal end 32a. Tube 28a is mounted coaxially within passageway 24a extending from the proximal end of the body to the distal end. Tube 28a has at least one side port 36a opening into the bore located a distance "x" distally from the closed end. Valve 26a includes a resilient member 40a located coaxially about tube 28a with a proximal surface 41a. Resilient member 40a is biased to occlude side port 36a in the normally closed position. The bias for valve 26a to its normally closed position is provided by resilient member 40a being compressed between the normally closed relaxed position and distal shoulder 22a by mounting a fluid handling device. Analogous to the opening of the preferred embodiment shown in FIG. 3, valve 26a is opened by distal compression of resilient member 40a, provided by a male luer fitting applied to proximal surface 41a when a fluid handling device is mounted onto the adapter, to provide the bias and to uncover side port 36a to allow a fluid flow through the valve. Resilient member 40a includes a proximal seal 70a to provide substantially continuous proximal surface 15a when the valve is closed and substantially prevent fluid from entering the chamber below the resilient member. In this embodiment, chamber 20a is dimensioned to provide clearance to allow for expansion of the resilient member when the member is compressed by the fluid handling device.

The valved adapter of the present invention is tolerant of male luer fittings at the extremes of the allowable tolerance in length and diameter provided for in the international standard. The tolerance is provided by the ability of resilient member 40 to be moved distally along tube 28. The side port is positioned and sized so that even a minimum length "fat" male luer opens the valve, and any additional length beyond what is need to open the valve present in a maximum length "thin" luer is allowed for by simply moving the resilient member further distally along tube 28. Since the fluid flow pathway is through bore 30 of the hollow tube, the fluid flow through the adapter is not impeded by additional displacement of the resilient member, even in the embodiment of FIG. 4, where the bias is provided by compression of resilient member 40a itself The resilient member is preferably formed from an elastomeric material having a Shore A Durometer between about 30 to about 100. Suitable elastomeric materials include, but are not limited to, natural rubber, silicone rubber, polychloroprene, polyvinylchloride, ethylene-propylene-diene-monomer (EPDM), polyurethane and the like. Preferably, the resilient member is formed from silicone rubber. Preferably, an inside diameter of the resilient member is slightly smaller than an outside diameter of tube 28. The difference in diameters produces an interference and provides a compression fit about the tube to substantially seal the openings when the valve is closed.

The adapter of the present invention, by having the resilient member close the side port of the tube as the resilient member returns to the normally closed position as the fluid handling device is removed, substantially eliminates the tendency of many valved adapters to spurt liquid present on the surface of the valve mechanism. Fluid handling devices preferably are attached to the valve adapter with a male luer fitting With the present invention, by the time a fluid handling device is fully removed from the adapter, the side port opening is already occluded. Additionally, because the volume of the liquid present on the surface of the resilient member is very small, there is substantially no spurting. The adapter of the present invention has an easily cleaned substantially continuous proximal surface that may be wiped substantially clean by a user when the fluid handling device is removed. The adapter of the present invention has substantially no "dead volume" between the normally closed valve and the proximal surface of the adapter, thereby substantially avoiding residual material that may support microbial growth or occlude the valve during periods when the valve is not in use. The adapter of the present invention provides a reliable and positive closure with an easily cleanable proximal surface providing benefits to the art of medical fluid transmission not previously available.

What is claimed is:

1. A valved adapter, comprising:

a body having a proximal end defining an opening therein, a distal end and a chamber extending therebetween;

a tube defining a lumen therein and having a closed proximal end, a side port in fluid communication with the lumen and an open distal end in fluid communication with the lumen, the tube being disposed in the chamber;

a resilient member having a proximal end and being coaxially disposed about the tube in the chamber and being moveable between a first condition wherein the proximal end of the resilient member is distal of the closed proximal end of the tube but where the proximal end of the resilient member is substantially flush with the proximal end of the body and the resilient member substantially fills the opening and occludes the side port and a second condition; and a biasing mechanism cooperating with the resilient member to bias the resilient member to its first condition.

2. The valved adapter of claim 1 wherein the biasing mechanism is a coil spring.

3. The valved adapter of claim 1 wherein the resilient member includes a reinforcement located coaxially about the tube.

4. The valved adapter of claim 3 wherein the reinforcement includes a guide flange to minimize misalignment of the resilient member during axial movement thereof.

5. The valved adapter of claim 4 wherein the biasing mechanism is a coil spring.

* * * * *